(12) United States Patent
Bodas et al.

(10) Patent No.: US 10,829,706 B2
(45) Date of Patent: Nov. 10, 2020

(54) CETANE-BOOSTING FUEL ADDITIVES, METHOD OF MANUFACTURE, AND USES THEREOF

(71) Applicant: SABIC Global Technologies B.V., Bergen op Zoom (NL)

(72) Inventors: Vijay Dinkar Bodas, Riyadh (SA); Sultan Eid Al-Otaibi, Riyadh (SA); Guillermo Leal, Riyadh (SA); Mohammed Bismillah Ansari, Riyadh (SA); Naif Mohammed Al Naddah Al-Otaibi, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/631,100

(22) PCT Filed: Jul. 17, 2018

(86) PCT No.: PCT/IB2018/055294
§ 371 (c)(1),
(2) Date: Jan. 14, 2020

(87) PCT Pub. No.: WO2019/016700
PCT Pub. Date: Jan. 24, 2019

(65) Prior Publication Data
US 2020/0157444 A1 May 21, 2020

Related U.S. Application Data

(60) Provisional application No. 62/534,293, filed on Jul. 19, 2017.

(51) Int. Cl.
| | | |
|---|---|---|
| *C10L 1/185* | (2006.01) | |
| *C07C 41/56* | (2006.01) | |
| *C10L 10/12* | (2006.01) | |
| *B01J 39/20* | (2006.01) | |

(52) U.S. Cl.
CPC .......... *C10L 1/1852* (2013.01); *C07C 41/56* (2013.01); *C10L 10/12* (2013.01); *B01J 39/20* (2013.01); *C10L 2200/0446* (2013.01)

(58) Field of Classification Search
CPC ........ C10L 1/185; C10L 1/1852; C10L 10/12; C10L 2200/0446; B01J 30/20; B01J 39/20
See application file for complete search history.

(56) References Cited

U.S. PATENT DOCUMENTS

| | | | |
|---|---|---|---|
| 3,036,904 A | 5/1962 | Chafetz et al. | |
| 6,013,114 A | 1/2000 | Hille et al. | |
| 2009/0100749 A1* | 4/2009 | Rabello | C10L 10/12 44/308 |
| 2015/0113859 A1* | 4/2015 | Voelkel | C10L 1/22 44/351 |
| 2015/0113867 A1* | 4/2015 | Voelkel | C08G 65/20 44/444 |
| 2016/0024411 A1 | 1/2016 | Arondel et al. | |

FOREIGN PATENT DOCUMENTS

| | | |
|---|---|---|
| EP | 0968259 B1 | 5/2000 |
| EP | 2987781 | 2/2016 |
| FR | 1576890 | 8/1969 |
| GB | 1107244 | 3/1968 |
| WO | 2012163935 A2 | 12/2012 |
| WO | 2017006141 | 1/2017 |

OTHER PUBLICATIONS

International Preliminary Report on Patentability for International Application No. PCT/IB2018/055294; International Filing Date: Jul. 17, 2018; dated Oct. 31, 2018; 7 pages.
"Fuel additives: A risk screening of additives to gasoline and diesel", Teknik og Administration Nr. 3 2006, 145 pages.
Clothier, P.Q.E. et al., "How do diesel-fuel ignition improvers work?", Chem. Soc. Reviews, (1993) 22, pp. 101-108.
International Search Report for International Application No. PCT/IB2018/055294; International Filing Date: Jul. 17, 2018; dated Oct. 31, 2018; 6 pages.
Schmitz, N. et al., "Reaction Kinetics of the Formation of Poly(oxymethylene) DimethylEthers from Formaldehyde and Methanol in Aqueous Solutions" Ind. Eng. Chem. Res. 2015, 54, 12553-12560.
Written Opinion of the International Searching Authority for International Application No. PCT/IB2018/055294; International Filing Date: Jul. 17, 2018; dated Oct. 31, 2018; 8 pages.

* cited by examiner

*Primary Examiner* — Ellen M McAvoy
(74) *Attorney, Agent, or Firm* — Cantor Colburn LLP

(57) ABSTRACT

A method of manufacturing a cetane-boosting fuel additive includes reacting formaldehyde and 2-ethylhexanol at a mole ratio of 10:1 to 1:1, or 5:1 to 1.5:1, or 4:1 to 2:1, or 3.5:1 to 2.5:1 in the presence of a heterogeneous acid catalyst at a temperature of 300 to 375° K to obtain a cetane-boosting product mixture comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3.

20 Claims, No Drawings

CETANE-BOOSTING FUEL ADDITIVES, METHOD OF MANUFACTURE, AND USES THEREOF

CROSS REFERENCE TO RELATED APPLICATIONS

This application is a National Stage application of PCT/IB2018/055294, filed Jul. 17, 2018, which is incorporated herein by reference in its entirety, and which claims the benefit of U.S. Provisional Application No. 62/534,293, filed Jul. 19, 2017.

BACKGROUND

This disclosure is directed to cetane-boosting fuel additives, a process for making the cetane-boosting fuel additives, and fuels containing the cetane-boosting fuel additives.

A Diesel engine is any internal-combustion engine in which air is compressed to a sufficiently high temperature to ignite diesel fuel injected into the cylinder, where combustion and expansion actuate a piston. Diesel engines have found broad use as a result of higher thermodynamic efficiency, and thus higher fuel efficiency.

In diesel engines, a mechanical injector system vaporizes the fuel directly into the combustion chamber or a precombustion chamber. This forced vaporization means that less-volatile fuels can be used. Because only air is inducted into the cylinder in a diesel engine, the compression ratio can be much higher as there is no risk of pre-ignition provided the injection process is accurately timed. This means that cylinder temperatures are much higher in a diesel engine than in a gasoline engine, allowing less volatile fuels to be used.

Diesel exhaust tends to be high in NOx and particulates, both visible (smoke) and invisible. Both NOx and particulates are significant environmental pollutants.

The term "diesel fuel" generally refers to any fuel for a compression ignition (diesel) engine. The most common type of diesel fuel is a specific fractional distillate of petroleum fuel oil, but alternatives that are not derived from petroleum, such as biodiesel, are increasingly being developed and adopted.

Some measurements of diesel fuel quality include cetane number, energy content, density, lubricity, cold-flow properties, and sulfur content. Cetane Number (CN) is an indicator of the time delay between injection and spontaneous ignition of a fuel in a standard diesel engine running under specified conditions. The shorter the ignition delay, the higher the cetane number.

Standard specifications for seven grades of petroleum-derived diesel fuel oils, suitable for various types of diesel engines, are addressed by ASTM D 975. The D 975 specification contains the minimum mandatory requirements needed to guarantee acceptable performance for the majority of users. In the United States, diesel-powered vehicles primarily use Grade No. 2-D diesel fuel, as designated by ASTM D-975. The European Union has also developed specifications, EN 590, for diesel fuels.

Additives, such as cetane-boosting additives, are used in diesel fuel for a wide variety of purposes including improving engine and fuel delivery system performance, improving fuel handling, improving fuel stability, and controlling contaminants. Cetane-boosting additives raise the cetane number of the fuel. Within a certain range, a higher cetane number can reduce combustion noise and smoke and enhance ease of starting the engine in cold climates.

Common commercial additives to raise the cetane number include alkyl nitrates and di-tert-butyl peroxide. 2-Ethylhexyl nitrate (EHN) is the most widely used cetane-boosting compound. EHN is thermally unstable and decomposes rapidly at the high temperatures in the combustion chamber. The products of decomposition help initiate fuel combustion and thus shorten the ignition delay period from that of the fuel without the additive. EHN is typically used in the concentration range from 0.05 to 0.4 percent mass and may yield a three to eight cetane number benefit. A disadvantage of EHN is that it decreases the thermal stability of some diesel fuels. Di-tertiary butyl peroxide (DTBP) is a less effective cetane-boosting compound than EHN, although DTBP does not degrade thermal stability of most diesel fuels. DTBP also does not contain nitrogen, which may be important for meeting some reformulated diesel fuel regulatory requirements.

With the rise of environmental concerns, the fuel industry has been driven to lessen emissions and increase performance. Europe, for instance, has implemented a minimum Cetane Number (51) in its diesel fuel specification (EN 590).

In view of the foregoing, there remains a need for improved cetane-boosting compositions, cost-effective methods for producing cetane-boosting compositions, and diesel fuel compositions comprising the cetane-boosting compositions.

BRIEF DESCRIPTION

A method of manufacturing a cetane-boosting fuel additive includes reacting formaldehyde and 2-ethylhexanol at a mole ratio of 10:1 to 1:1, or 5:1 to 1.5:1, or 4:1 to 2:1, or 3.5:1 to 2.5:1 in the presence of a heterogeneous acid catalyst at a temperature of 300 to 375° K to obtain a cetane-boosting product mixture comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3.

Accordingly, a cetane-boosting fuel additive comprises $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3.

In another embodiment, a method of manufacturing a cetane-boosting fuel additive comprises reacting formaldehyde and 2-ethylhexanol at a mole ratio of 3.5:1 to 2.5:1 in the presence of a sulfonated polystyrene cation exchange resin catalyst at a temperature of 300 to 375° K to obtain a cetane-boosting product mixture comprising the hemiacetal $H_3C(CH_2)_3CH(CH_2CH_3)CH_2(OCH_2)_nOH$, the acetal $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3, formaldehyde, and 2-ethylhexanol; and separating the cetane-boosting fuel additive from the product mixture.

Also disclosed is a cetane-boosting fuel additive made by any of these methods.

A diesel fuel composition comprises 90 to 99.98 volume percent of a diesel fuel; 0.02 to 10 volume percent of the cetane-boosting fuel additive; wherein the diesel fuel composition has a higher Cetane Number, derived from Ignition Quality testing in accordance with ASTM D 6890, than the diesel fuel without the cetane-boosting fuel additive.

A method of manufacturing a diesel fuel composition comprises adding to a diesel fuel 0.02 to 10 volume percent of the cetane-boosting fuel additive.

The above described and other features are exemplified by the following detailed description, examples, and claims.

DETAILED DESCRIPTION

Described herein are cetane-boosting fuel additives, processes for manufacturing the cetane-boosting fuel additives, and diesel fuel compositions comprising the cetane-boosting fuel additives. The cetane-boosting fuel additives have high oxygen content, cetane number and good solubility in diesel fuel, an advantageous combination of attributes for a cetane-boosting fuel additive for diesel fuel compositions, particularly for the automotive market.

The cetane-boosting fuel additive comprises the hemiacetal $H_3C(CH_2)_3CH(CH_2CH_3)CH_2(OCH_2)_nOH$, the acetal $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3.

The cetane-boosting fuel additive can be manufactured by reacting 2-ethylhexanol ($H_3C(CH_2)_3CH(CH_2CH_3)CH_2OH$) and formaldehyde (HCHO) in the presence of a heterogeneous acid catalyst, for example a cation exchange resin. The formaldehyde can oligomerize in 2-ethylhexanol, for example according to the reaction Equations (1) to (3) shown below, to form a population of hemiacetals upon continued addition of formaldehyde.

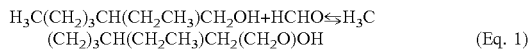

(Eq. 1)

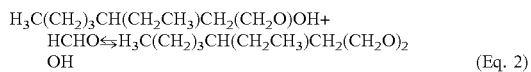

(Eq. 2)

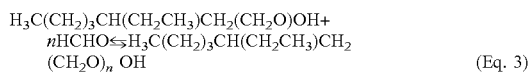

(Eq. 3)

The corresponding acetals (2-ethylhexanol diethers) can also be formed in the reaction mixture, for example as shown in Equation 4.

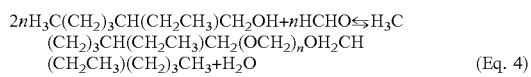

(Eq. 4)

Other products of the reaction include glycols, e.g., $HOCH_2OH$, $HO(CH_2O)_2H$, n, and the like.

In the above formulas, n is the average degree of oligomerization of the formaldehyde groups in the products. The reaction can yield a population of the hemiacetal $H_3C(CH_2)_3CH(CH_2CH_3)CH_2(CH_2O)_nOH$ with n=2 to 8, for example, but with an average oligomerization degree of n=3. The value of n can be controlled by reaction conditions, in particular the mole ratio of formaldehyde and 2-ethylhexanol, reaction temperature, and pressure, and reaction time. For example, a mole ratio of formaldehyde to 2-ethylhexanol in the reaction can be 10:1 to 1:1, or 5:1 to 1.5:1, or 4:1 to 2:1, or 3.5:1 to 2.5:1, and reaction conditions can be adjusted accordingly to achieve the desired average value of n, where a higher temperature or a longer reaction time provides a higher average value of n. In an embodiment, a mole ratio of formaldehyde to 2-ethylhexanol is used that is effective to yield an average value of n of 2.8 to 3.2, preferably an average value of 3.

The compound 2-ethylhexanol is of the formula

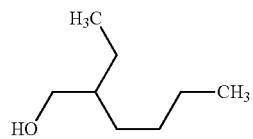

and can be in the form of an isolated, purified compound, or can be a purified or crude product of a 2-ethylhexanol production process.

The formaldehyde can be in the form of an isolated, purified compound, or can be a purified or crude product or by-product of a chemical process. The formaldehyde can be provided as a solution (e.g., as formalin or formol), as a gas, or as a reactive derivative, for example as paraformaldehyde. Gaseous monomeric formaldehyde can be obtained by thermally decomposing paraformaldehyde in an inert non-volatile liquid carrier at a temperature of 175 to 200° C. It is also possible to use hemiformals of formaldehyde with a lower alcohol such as methanol.

The catalyst is a heterogeneous acid catalyst. The term "heterogeneous" as used herein with respect to solid catalysts, refers to any solid physical form of suitable catalyst, whether a catalyst is calcined or otherwise hardened, whether provided in powder, pellet, balled, or extruded form or anchored to a solid structure such as a molecular sieve or natural or synthetic solid state composition. Such catalysts are generally not solubilized during the reaction and the majority of the catalyst is recoverable from the reaction products by simple filtration. An exemplary heterogeneous acid catalyst is a cation exchange resin. A preferred cation exchange resin is a sulfonated polystyrene resin. The amount of the catalyst is more than 0 to 2 weight percent (wt. %), based on the total weight of the formaldehyde and the 2-ethylhexanol, for example 0.05 to 1.5 wt. %.

The temperature, pressure, and time of the reaction can vary depending on the molar ratio of the reactants, the desired value of n, and other desired parameters. For example, higher temperature and pressure can lead to a shorter reaction time. The temperature for the reaction can be from 275 to 398° K, or 300 to 375° K. The pressure for the reaction can be from 0.5 bar (50% vacuum, 0.05 mega-Pascal (MPa)) to 2 bar (0.2 MPa), preferably 0.8 bar to 1.2 bar (0.08 to 0.12 MPa). The time for the reaction can be 10 minutes to 6 hours, for example 30 minutes to 3 hours.

The reaction can be conducted in the atmosphere or under an inert atmosphere, for example under nitrogen or argon.

The method further can comprise isolating the cetane-boosting fuel additive compounds from the product mixture, which can contain the hemiacetal, the acetal, residual formaldehyde, 2-ethyl hexanol, glycols, water, and other by-products. Isolating the cetane-boosting fuel additive compounds can include a series of process steps including one or more of distillation, acid neutralization, and filtration, which can be conducted in any order. In an embodiment, the product mixture is distilled to remove at least a portion of the residual formaldehyde, water, a by-product, or a combination thereof. Distillation can be conducted so as to remove these components sequentially or at the same time.

The reaction can be conducted in two or more successive stages, for example involving the sequential addition of two or more portions of the formaldehyde. The reaction or the reaction and the isolation can be conducted in equipment such as stirred tank reactors in a continuous or batch process. The reactor can be fitted with inlets for the reactants, and an outlet for product, where the outlet can be connected to a distillation column or other distillation apparatus. Alternatively, the reaction can be conducted in a fixed bed reactor containing the catalyst where a stream comprising the reactants is passed over and through the bed in a continuous or batch process. The product stream can then be removed and the product cetane-boosting fuel additive isolated.

CN can be measured for each cetane-boosting fuel additive disclosed herein or for each diesel fuel composition comprising the cetane-boosting fuel additive.

CN is an inverse function of a fuel's ignition delay, and the time period between the start of injection and the first identifiable pressure increase during combustion of the fuel. CN of diesel fuel can be derived by measurement in the Ignition Quality Tester (IQT) according to ASTM D 6890.

CN can also be calculated for cetane-boosting compounds using methods such as those in the Los Alamos report LA-UR-16-25529, "A group contribution method for estimating cetane and octane numbers," William Louis Kubic, issued 2016 Jul. 28.

The cetane number characterizing the cetane-boosting fuel additive disclosed herein is expected to be high. Further advantages of the cetane-boosting fuel additive are that it is compatible with diesel fuels and the compounds do not include any nitrogen. These properties make the cetane-boosting fuel additive an attractive candidate as a diesel fuel additive.

Also disclosed is a diesel fuel composition comprising a diesel fuel and a cetane-boosting fuel additive disclosed herein, wherein the diesel fuel composition has a higher CN, determined in accordance with ASTM D 6890, than the diesel fuel without the cetane-boosting fuel additive. The diesel fuel composition can have a CN that is 0.5 to 20, or 1 to 15, or 1.5 to 10 points higher than the CN of the diesel fuel without the cetane-boosting fuel additive.

In the diesel fuel composition, the diesel fuel is present in an amount of 60 to 99.8 volume percent (vol. %), or 65 to 99 vol. %, or 70 to 99.8 vol. %, or 75 to 95 vol. %, each based on the total volume of the diesel fuel composition. The cetane-boosting fuel additive can be present in the diesel fuel composition in an amount of 0.2 to 20 vol. %, or 0.3 to 15 vol. %, or 0.4 to 10 vol. %, or 0.5 to 7.5 vol. %, each based on the total volume of the diesel fuel composition.

The diesel fuel composition can be prepared by combining a diesel fuel and the components of a cetane-boosting fuel additive disclosed herein, either separately or in any combination.

The cetane-boosting fuel additive or components thereof can be added directly to the diesel fuel. However, the cetane-boosting fuel additive or components thereof can be diluted with a substantially inert, normally liquid organic diluent such as mineral oil, naphtha, benzene, toluene, xylene, or alcohols such as 2-ethylhexanol, decanol, and isotridecanol to form an additive concentrate. These concentrates can comprise 0.1 to 80% by weight, or 1% to 80% by weight, or 10% to 80% by weight, of the cetane-boosting fuel additive and can contain, in addition, one or more other additives known in the art as described below. Concentrations such as 15%, 20%, 30% or 50% or higher can be used. The concentrates can be prepared by combining the desired components in any order at any temperature, for example at 23 to 70° C.

The cetane-boosting fuel additive or the diesel fuel composition can further comprise other additives known in the art, for example injector cleanliness additives (detergents), lubricity additives, smoke suppressants, anti-foam agents (e.g. polyether-modified polysiloxanes), anti-icing agents, low temperature operability agents, conductivity agents, drag-reducing additives, anti-oxidants (e.g. phenolics such as 2,6-di-tert-butylphenol, or phenylenediamines such as N,N'-di-sec-butyl-p-phenylenediamine), metal deactivators, stabilizers, dispersants, biocides, de-emulsifiers, corrosion inhibitors, dyes, and the like. The amounts of such additives depend on the particular additive, and can be readily determined by one of ordinary skill in the art. In general, the individual additives can each be present in an amount of 1 to 800, or 5 to 500 parts per million parts of the diesel fuel composition, each by weight (ppm). For example, anti-oxidants can be present in an amount of 10 to 800 ppm, dispersants can be present in an amount of 15 to 100 ppm, and stabilizers can be present in an amount of 50 to 150 ppm.

Lubricity additives are used to compensate for the lower lubricity of severely hydrotreated diesel fuels. Suitable lubricity improvers or friction modifiers are based typically on fatty acids or fatty acid esters, such as glyceryl monooleate, triglycerides, and alkanolamines.

Ashless polymeric detergent additives can clean up fuel injector deposits and/or keep injectors clean. These additives are composed of a polar group that bonds to deposits and deposit precursors, and a non-polar group that dissolves in the fuel. Thus, the additive can redissolve deposits that already have formed and reduce the opportunity for deposit precursors to form deposits. Examples of detergents suitable for use include polyolefin substituted succinimides or succinamides of polyamines, for instance polyisobutylene succinimides or polyisobutylene amine succinamides, aliphatic amines, Mannich bases or amines, and polyolefin (e.g. polyisobutylene) maleic anhydrides.

Corrosion inhibitors are compounds that attach to metal surfaces and form a protective barrier that prevents attack by corrosive agents. For example, corrosion inhibitors can include succinic esters, in particular with polyols, fatty acid derivatives, for example oleic esters, oligomerized fatty acids, and substituted ethanolamines. Corrosion inhibitors can be present in an amount of 5 to 15 ppm.

De-emulsifiers (also known as demulsifiers) are surfactants that break up emulsions and allow fuel and water to separate. Demulsifiers include the alkali metal or alkaline earth metal salts of alkyl-substituted phenol- and naphthalene sulfonates and the alkali metal or alkaline earth metal salts of fatty acids, and also neutral compounds such as alcohol alkoxylates, e.g. alcohol ethoxylates, phenol alkoxylates, e.g. tert-butylphenol ethoxylate or tert-pentylphenol ethoxylate, fatty acids, alkylphenols, condensation products of ethylene oxide (EO) and propylene oxide (PO), including in the form of EO/PO block copolymers, polyethyleneimines, or polysiloxanes. Demulsifiers can be present in an amount of 5 to 30 ppm.

Metal deactivators include salicylic acid derivatives such as N,N'-disalicylidene-1,2-propanediamine. Metal deactivators can be present in an amount of 1 to 15 ppm.

This disclosure is further illustrated by the following examples, which are non-limiting.

EXAMPLES

Example 1. Preparing a Cetane-Boosting Additive from Formaldehyde and 2-Ethylhexanol Cetane boosters are prepared by mixing formaldehyde with 2-ethylhexanol in a 3 to 1 mole ratio. The mixture is then passed over a conventional cation exchange resin, for example a sulfonated polystyrene resin, at a temperature of 300 to 375° K and atmospheric pressure to obtain a cetane-boosting product mixture comprising $H_3C(CH_2)_3CH(CH_2CH_3)CH_2(CH_2O)_3OH$ wherein n has an average value of 3.

Example 2. Cetane Number for Cetane-Boosting Additive

The cetane number of each of the species in the cetane-boosting product mixture of Example 1 can be predicted by the methods in Los Alamos report LA-UR-16-25529, "A group contribution method for estimating cetane and octane numbers," William Louis Kubic, 2016 Jul. 28.

The cetane number for $H_3C(CH_2)_3CH(CH_2CH_3)CH_2(CH_2O)_nOH$ wherein n has an average value of 3 is predicted to be 99.48.

This disclosure further encompasses the following embodiments.

Embodiment 1

A method of manufacturing a cetane-boosting fuel additive, the method comprising reacting formaldehyde and 2-ethylhexanol at a mole ratio of 10:1 to 1:1, or 5:1 to 1.5:1, or 4:1 to 2:1, or 3.5:1 to 2.5:1 in the presence of a heterogeneous acid catalyst at a temperature of 300 to 375° K to obtain a cetane-boosting product mixture comprising $H_3C(CH_2)_3CH(CH_2CH_3)CH_2(OCH_2)_nOH$ wherein n has an average value of 2.8 to 3.2, preferably an average value of 3.

Embodiment 2

The method of embodiment 1, wherein the heterogeneous acid catalyst comprises a cation exchange resin.

Embodiment 3

The method of embodiment 2, wherein the cation exchange resin is a sulfonated polystyrene.

Embodiment 4

The method of any one or more of embodiments 1 to 3, wherein the catalyst is present in an amount of more than 0 to 2 weight percent, based on the total weight of the formaldehyde and the 2-ethylhexanol.

Embodiment 5

The method of any one or more of embodiments 1 to 4, wherein the cetane-boosting product mixture further comprises formaldehyde, 2-ethylhexanol, or a combination comprising formaldehyde and 2-ethylhexanol.

Embodiment 6

The method of any one or more of embodiments 1 to 5, further comprising separating the catalyst and the product mixture to provide the cetane-boosting fuel additive.

Embodiment 7

The method of any one or more of embodiments 5 to 6, further comprising at least partially removing the formaldehyde, the 2-ethylhexanol, or both to provide the cetane-boosting fuel additive.

Embodiment 8

A method of manufacturing a cetane-boosting fuel additive, the method comprising reacting formaldehyde and 2-ethylhexanol at a mole ratio of 3.5:1 to 2.5:1, in the presence of a sulfonated polystyrene cation exchange resin catalyst at a temperature of 300 to 375° K to obtain a cetane-boosting product mixture comprising $H_3C(CH_2)_3CH(CH_2CH_3)CH_2(OCH_2)_nOH$ wherein n has an average value of 2.8 to 3.2, preferably an average value of 3, formaldehyde, and 2-ethylhexanol; and separating the catalyst and the cetane-boosting product mixture to provide the cetane-boosting fuel additive.

Embodiment 9

The method of embodiment 8, further comprising removing at least a portion of the formaldehyde, the 2-ethylhexanol, or both to provide the cetane-boosting fuel additive.

Embodiment 10

A cetane-boosting fuel additive made by the method of any one or more of embodiments 1 to 9.

Embodiment 11

A diesel fuel composition comprising 90 to 99.98 volume percent of a diesel fuel; and 0.02 to 10 volume percent of a cetane-boosting fuel additive comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3; wherein the diesel fuel composition has a higher Cetane Number, derived from Ignition Quality testing in accordance with ASTM D 6890, than the diesel fuel without the cetane-boosting fuel additive.

Embodiment 12

The diesel fuel composition of embodiments 11, wherein the cetane-boosting fuel additive is made by the method of any one or more of embodiments 1 to 9.

Embodiment 13

A method of manufacturing a diesel fuel composition comprising adding to a diesel fuel 0.02 to 10 volume percent of a cetane-boosting fuel additive comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3.

Embodiment 14

The method of embodiment 13, wherein the cetane-boosting fuel additive is made by the method of any one or more of embodiments 1 to 9.

Embodiment 15

A cetane-boosting fuel additive comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2, preferably an average value of 3.

The additives, compositions, and methods can alternatively comprise, consist of, or consist essentially of, any appropriate materials, steps, or components herein disclosed. The additives, compositions, and methods can additionally, or alternatively, be formulated so as to be devoid, or substantially free, of any materials (or species), steps, or components, that are otherwise not necessary to the achievement of the function or objectives of the additives, compositions, and methods.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of manufacturing a cetane-boosting fuel additive, the method comprising
reacting formaldehyde and 2-ethylhexanol at a mole ratio of 10:1 to 1:1 in the presence of a heterogeneous acid catalyst at a temperature of 300 to 375° K to obtain a cetane-boosting product mixture comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2.

2. The method of claim 1, wherein the heterogeneous acid catalyst comprises a cation exchange resin.

3. The method of claim 2, wherein the cation exchange resin is a sulfonated polystyrene.

4. The method of claim 1, wherein the catalyst is present in an amount of more than 0 to 2 weight percent, based on the total weight of the formaldehyde and the 2-ethylhexanol.

5. The method of claim 1, wherein the cetane-boosting product mixture further comprises formaldehyde, 2-ethylhexanol, or a combination comprising formaldehyde and 2-ethylhexanol.

6. The method of claim 1, further comprising
separating the catalyst and the cetane-boosting product mixture to provide the cetane-boosting fuel additive.

7. The method of claim 5, further comprising removing at least a portion of the formaldehyde, the 2-ethylhexanol, or both to provide the cetane-boosting fuel additive.

8. A cetane-boosting fuel additive made by the method of claim 1.

9. The method of claim 6, further comprising removing at least a portion of the formaldehyde, the 2-ethylhexanol, or both to provide the cetane-boosting fuel additive.

10. The method of claim 1,
wherein the catalyst is present in an amount of more than 0 to 2 weight percent, based on the total weight of the formaldehyde and the 2-ethylhexanol;
wherein the cetane-boosting product mixture further comprises formaldehyde, 2-ethylhexanol, or a combination comprising formaldehyde and 2-ethylhexanol;
further comprising separating the catalyst and the cetane-boosting product mixture to provide the cetane-boosting fuel additive; and
further comprising removing at least a portion of the formaldehyde, the 2-ethylhexanol, or both to provide the cetane-boosting fuel additive.

11. The method of claim 1, wherein reacting formaldehyde and 2-ethylhexanol is at a mole ratio of 5:1 to 1.5:1; and
wherein n has an average value of 3.

12. The method of claim 1, wherein reacting formaldehyde and 2-ethylhexanol is at a mole ratio of 3.5:1 to 2.5:1.

13. A method of manufacturing a cetane-boosting fuel additive, the method comprising
reacting formaldehyde and 2-ethylhexanol at a mole ratio of 3.5:1 to 2.5:1, in the presence of a sulfonated polystyrene cation exchange resin catalyst at a temperature of 300 to 375° K to obtain a cetane-boosting product mixture comprising $H_3C(CH_2)_3CH(CH_2CH_3)CH_2(OCH_2)_nOH$ wherein n has an average value of 2.8 to 3.2, formaldehyde, and 2-ethylhexanol; and
separating the catalyst and the cetane-boosting product mixture to provide the cetane-boosting fuel additive.

14. The method of claim 13, further comprising removing at least a portion of the formaldehyde, the 2-ethylhexanol, or both to provide the cetane-boosting fuel additive; and
wherein n has an average value of 3.

15. A cetane-boosting fuel additive comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2.

16. A diesel fuel composition comprising
90 to 99.98 volume percent of a diesel fuel; and
0.02 to 10 volume percent of the cetane-boosting fuel additive of claim 15 comprising $H_3C(CH_2)_3CH(CH_2CH_3)CH_2(OCH_2)_nOH$, $H_3C(CH_2)_3CH(CH_2CH_3)$ $CH_2(OCH_2)_nOCH_2CH(CH_2CH_3)(CH_2)_3CH_3$, or a combination thereof, and wherein n has an average value of 2.8 to 3.2;

wherein the diesel fuel composition has a higher Cetane Number, derived from Ignition Quality testing in accordance with ASTM D 6890, than the diesel fuel without the cetane-boosting fuel additive.

17. The diesel fuel composition of claim 16, wherein the cetane-boosting fuel additive is made by reacting formaldehyde and 2-ethylhexanol at a mole ratio of 10:1 to 1:1 in the presence of a heterogeneous acid catalyst at a temperature of 300 to 375° K to obtain a cetane-boosting product mixture comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2.

18. A method of manufacturing a diesel fuel composition comprising adding to a diesel fuel 0.02 to 10 volume percent of the cetane-boosting fuel additive of claim 15 comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, and wherein n has an average value of 2.8 to 3.2.

19. The method of claim 18, wherein the cetane-boosting fuel additive is made by reacting formaldehyde and 2-ethylhexanol at a mole ratio of 10:1 to 1:1 in the presence of a heterogeneous acid catalyst at a temperature of 300 to 375° K to obtain a cetane-boosting product mixture comprising $H_3C(CH_2)_3CH(CH_2CH_3)CH_2(OCH_2)_nOH$, $H_3C(CH_2)_3CH(CH_2CH_3)CH_2(OCH_2)_nOCH_2CH(CH_2CH_3)(CH_2)_3CH_3$, or a combination thereof, wherein n has an average value of 2.8 to 3.2.

20. The method of claim 19, wherein reacting formaldehyde and 2-ethylhexanol is at a mole ratio of 5:1 to 1.5:1; and wherein n has an average value of 3.

\* \* \* \* \*